United States Patent
Sueyasu

(10) Patent No.: US 10,058,232 B2
(45) Date of Patent: Aug. 28, 2018

(54) TRANSMISSION MECHANISM, RAISING DEVICE, AND INSERTION APPARATUS

(71) Applicant: OLYMPUS CORPORATION, Tokyo (JP)

(72) Inventor: Hidetada Sueyasu, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 3 days.

(21) Appl. No.: 15/269,391

(22) Filed: Sep. 19, 2016

(65) Prior Publication Data

US 2017/0000316 A1   Jan. 5, 2017

Related U.S. Application Data

(63) Continuation of application No. PCT/JP2015/071986, filed on Aug. 3, 2015.

(30) Foreign Application Priority Data

Aug. 25, 2014 (JP) .................. 2014-170696

(51) Int. Cl.
| | |
|---|---|
| *A61B 1/00* | (2006.01) |
| *A61B 1/018* | (2006.01) |
| *F16H 21/44* | (2006.01) |
| *G02B 23/24* | (2006.01) |
| *A61B 1/04* | (2006.01) |
| *A61B 17/00* | (2006.01) |

(52) U.S. Cl.
CPC ............ *A61B 1/00098* (2013.01); *A61B 1/00* (2013.01); *A61B 1/00066* (2013.01); *A61B 1/018* (2013.01); *F16H 21/44* (2013.01); *G02B 23/2476* (2013.01); *A61B 2017/0034* (2013.01); *A61B 2017/00323* (2013.01)

(58) Field of Classification Search
CPC . A61B 1/00098; A61B 1/00066; A61B 1/018; A61B 17/0034; A61B 17/00323; G02B 23/2476; F16H 21/44
See application file for complete search history.

(56) References Cited

FOREIGN PATENT DOCUMENTS

| CN | 1816262 A | 8/2006 |
|---|---|---|
| CN | 201010665 Y | 1/2008 |
| CN | 101457805 A | 6/2009 |
| DE | 10 2005 046 060 A1 | 3/2007 |

(Continued)

OTHER PUBLICATIONS

Chinese Office Action dated Jul. 3, 2017 in Chinese Patent Application No. 201580016344.4.

(Continued)

*Primary Examiner* — Timothy J Neal
(74) *Attorney, Agent, or Firm* — Scully, Scott, Murphy & Presser, P.C.

(57) ABSTRACT

A transmission mechanism includes a mobile member, and an adjustment unit which is coupled to the mobile member and which changes in an adjustment amount in a longitudinal axis C direction. The transmission mechanism further includes a pulling and pressing member which is coupled to the raising stand and the adjustment unit. The transmission mechanism further includes a regulation portion which regulates the adjustment amount of the adjustment unit when a raising operation portion is operated and when a tension is applied to the adjustment unit.

15 Claims, 8 Drawing Sheets

(56) References Cited

FOREIGN PATENT DOCUMENTS

| JP | 2003-245248 A | 9/2003 |
|----|---------------|--------|
| JP | 2003-305002 A | 10/2003 |

OTHER PUBLICATIONS

English translation of International Preliminary Report on Patentability dated Mar. 9, 2017 together with the Written Opinion received in related International Application No. PCT/JP2015/071986.
International Search Report dated Oct. 27, 2015 issued in PCT/JP2015/071986.
Chinese Office Action dated Jan. 29, 2018 in Chinese Patent Application No. 201580016344.4.

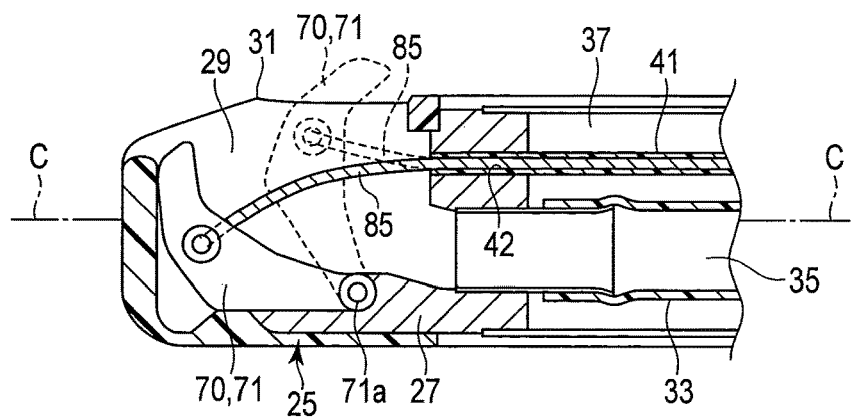
F I G. 1B
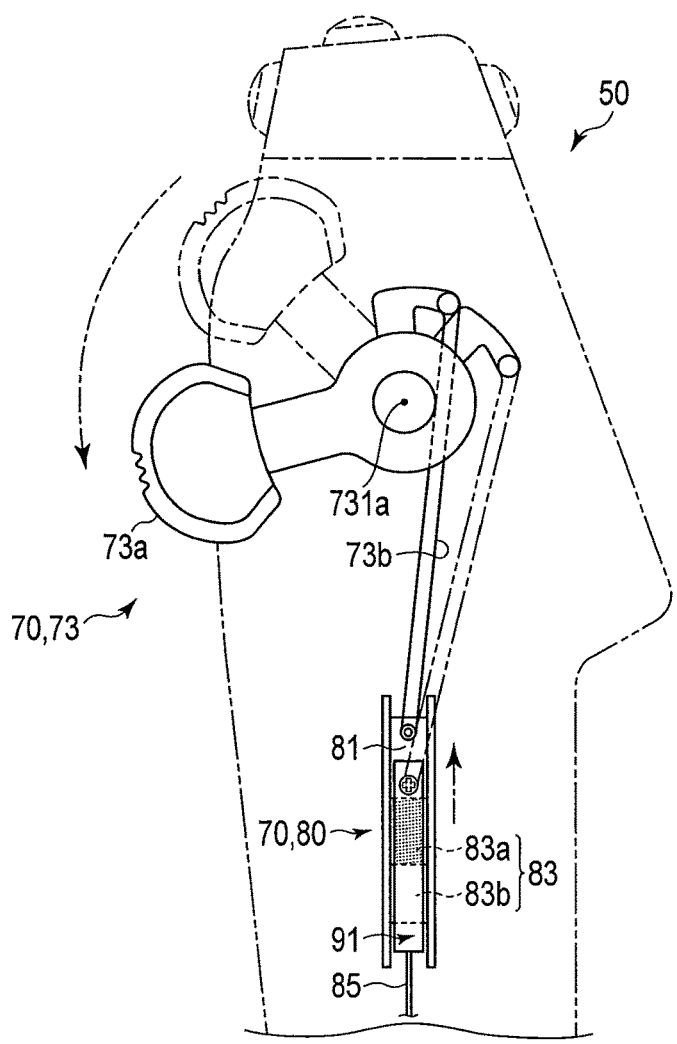
F I G. 1C

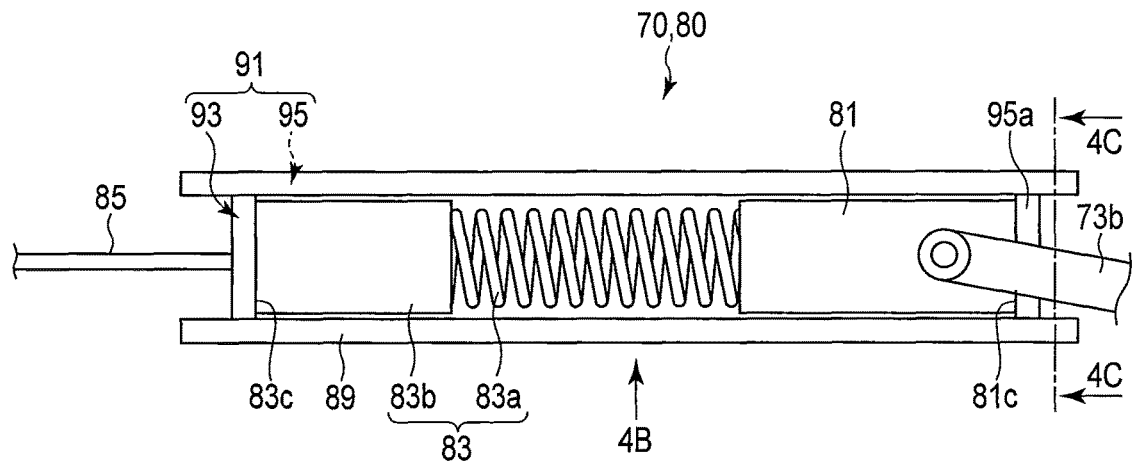
F I G. 4A
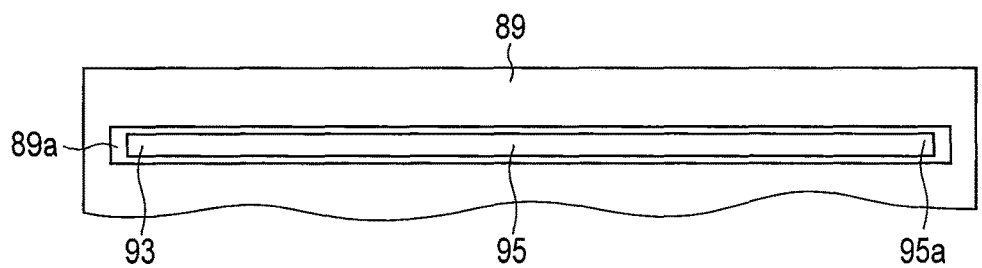
F I G. 4B
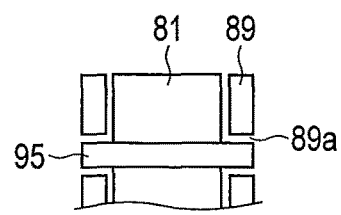
F I G. 4C

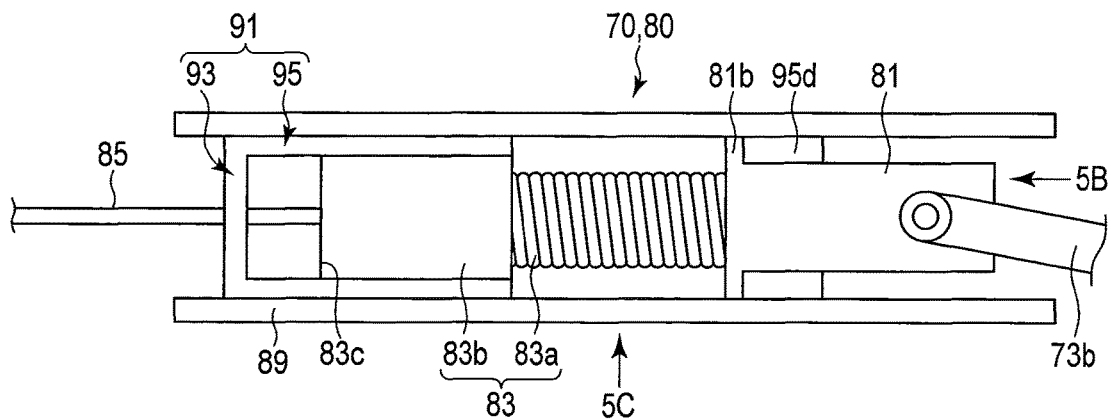
F I G. 5A
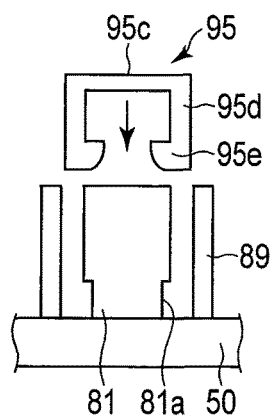
F I G. 5B
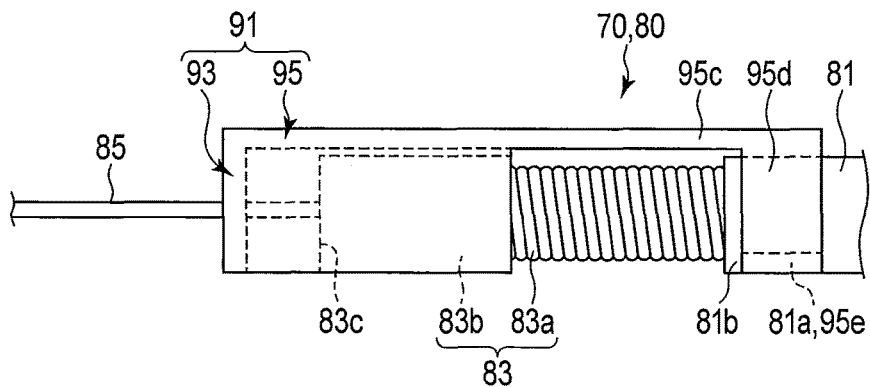
F I G. 5C

TRANSMISSION MECHANISM, RAISING DEVICE, AND INSERTION APPARATUS

CROSS-REFERENCE TO RELATED APPLICATIONS

This application is a Continuation application of PCT Application No. PCT/JP2015/071986, filed Aug. 3, 2015 and based upon and claiming the benefit of priority from prior Japanese Patent Application No. 2014-170696, filed Aug. 25, 2014, the entire contents of all of which are incorporated herein by reference.

BACKGROUND OF THE INVENTION

1. Field of the Invention

The present invention relates to a transmission mechanism which transmits an operational force of a raising operation portion to a raising stand to raise the raising stand that raises an insert object, a raising device having the transmission mechanism, and an insertion apparatus having the raising device.

2. Description of the Related Art

For example, a treatment instrument and a guide member which guides the treatment instrument to a subject function as an insert object to be inserted into an insertion portion of an endoscope.

In the endoscope, the insert object is mounted on a raising stand, and protrudes toward the lateral side of the insertion portion from a distal opening portion. In this state, the raising stand is raised by the operation of a raising operation portion, whereby the insert object comes closer to the subject, and becomes able to treat the subject. The thickness and hardness of the insert object vary according to purposes.

When a thin insert object or a soft insert object is used, the raising stand can raise to a maximum angle with small force even if the insert object is mounted on the raising stand. However, when a thick insert object or a hard insert object is used, the raising stand only raises halfway due to the thickness or hardness if the insert object is mounted on the raising stand. Much force is needed for the raising stand to raise to the maximum. In this case, members constituting a transmission mechanism such as a wire member to raise the raising stand are loaded by the great force.

For example, in Jpn. Pat. Appln. KOKAI Publication No. 2003-245248, an adjustment unit of a transmission mechanism has an expansion and contraction member which is coupled to a slider mechanism and a proximal end portion of an operation wire. The expansion and contraction member is a coil spring which expands and contracts to adjust the distance between the slider mechanism and the proximal end portion of the operation wire. The expansion and contraction member prevents breakage of the transmission mechanism by the adjustment of the distance. The expansion and contraction member also adjusts the raise angle of the raising stand by the adjustment of the distance.

BRIEF SUMMARY OF THE INVENTION

An aspect of a transmission mechanism of the present invention is a transmission mechanism which is coupled to a raising stand and a raising operation portion and which transmits an operational force of the raising operation portion to the raising stand to raise the raising stand, the raising stand rising to raise an insert object to be inserted into an insertion portion from an opening portion provided in the insertion portion, the raising operation portion operating the raising stand, includes a mobile member which moves forward and backward along an axial direction of the transmission mechanism by an operation of the raising operation portion; an adjustment unit which is coupled to the mobile member and thus moves forward and backward along the axial direction together with the mobile member and which varies in an adjustment amount in the axial direction; a pulling and pressing member which is coupled to the raising stand and the adjustment unit in a state where tension adjusted by the adjustment amount is acting thereon and which pulls or presses the raising stand; and a regulation portion which regulates the adjustment amount of the adjustment unit when the raising operation portion is operated and when the tension is applied to the adjustment unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1B is sectional view of a distal end hard portion schematically showing an example of a configuration of a distal end portion;

FIG. 1C is a diagram schematically showing configurations of a raising operation portion and a coupling member;

FIG. 4A is a top view of the transmission mechanism according to a first modification of the second embodiment;

FIG. 4B is a side view of the guide member and the transmission mechanism viewed from an arrow 4B side indicated in FIG. 4A;

FIG. 4C is a front view of the guide member and the transmission mechanism viewed from an arrow 4C side indicated in FIG. 4A;

FIG. 5A is a top view of the transmission mechanism in which a top view of the regulation portion according to a third embodiment is omitted;

FIG. 5B is a diagram showing the attachment of a support portion to a mobile member when viewed from an arrow 5B side indicated in FIG. 5A;

FIG. 5C is a side view of the transmission mechanism viewed from an arrow 5C side indicated in FIG. 5A in a state where a guide member shown in FIG. 5A is removed;

DETAILED DESCRIPTION OF THE INVENTION

Hereinafter, embodiments of the present invention will be described in detail with reference to the drawings.

[First Embodiment]
[Configuration]

The first embodiment is described with reference to FIG. 1A, FIG. 1B, FIG. 1C, FIG. 2A, FIG. 2B, FIG. 2C, and FIG. 2D. In some of the drawings, some components are not shown for clarification of the drawings.

[Insertion Apparatus 10]

Figure 1A:
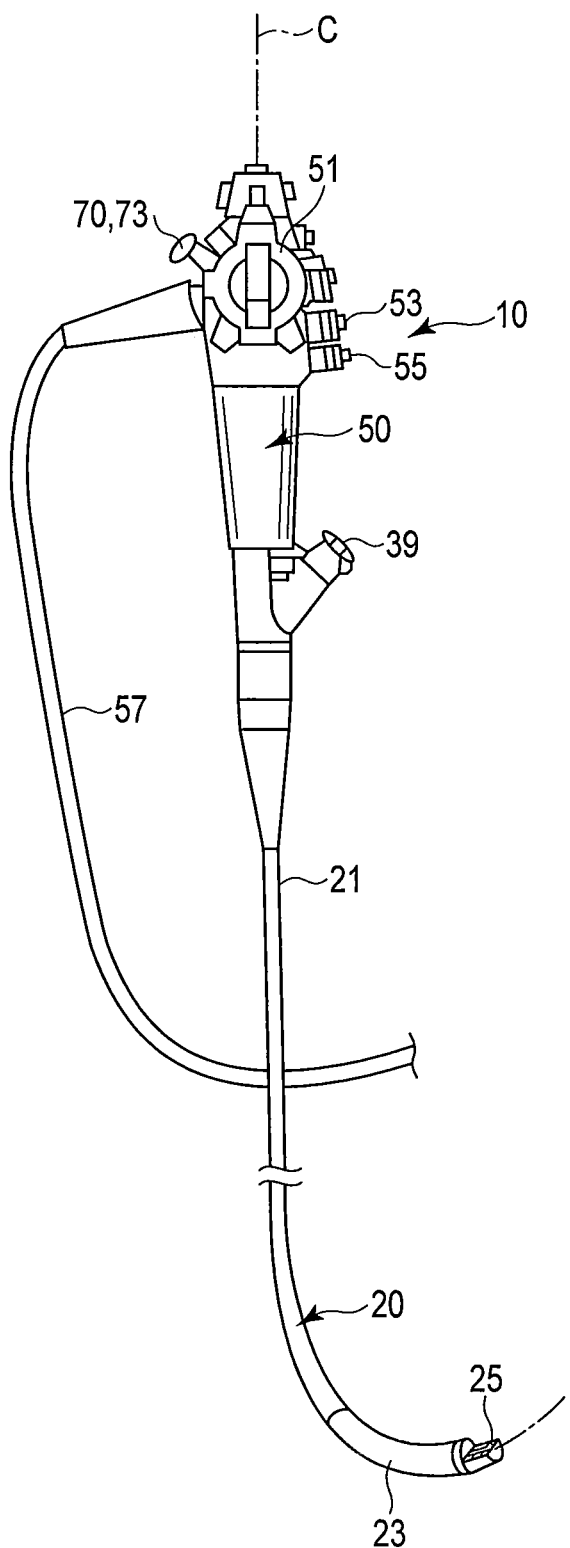
FIG. 1A is a schematic diagram of an insertion apparatus according to a first embodiment of the present invention.

An insertion apparatus 10 shown in FIG. 1A functions as, for example, an endoscope to be inserted into a lumen inside a body cavity. The insertion apparatus 10 according to the present embodiment is, for example, a side-view type endoscope which inserts a treatment instrument into a duodenal papilla or a biliary and pancreatic area. The insertion apparatus 10 according to the present embodiment may be a direct-view type endoscope, or may be an endoscope which inserts the treatment instrument into parts other than the aforementioned parts.

The insertion apparatus 10 according to the present embodiment is described as, for example, a medical endoscope, but does not need to be limited to this. It is also preferable that the insertion apparatus 10 be an industrial endoscope, or, for example, an insertion tool including a catheter and an over tube having no illumination optical system and no observation optical system, instead of the medical endoscope.

In the present embodiment, for example, an unshown treatment instrument to be inserted into an insertion portion 20 of the above insertion apparatus 10, and an unshown guide member which guides the treatment instrument to a subject are referred to as an insert object.

As shown in FIG. 1A, the insertion apparatus 10 has a longitudinal axis C. The insertion apparatus 10 has the insertion portion 20 extending along the longitudinal axis C direction, and a holding portion 50 provided at the proximal end portion of the insertion portion 20.

As shown in FIG. 1A, the insertion portion 20 has a flexible tube portion 21 which is coupled to the holding portion 50 and which has flexibility, a bendable portion 23 which is provided at a distal end of the flexible tube portion 21 and which can bend relative to the longitudinal axis C, and a distal end hard portion 25 which is provided at a distal end of the bendable portion 23.

As shown in FIG. 1B, the distal end hard portion 25 has a hard portion main body 27, and the hard portion main body 27 has a space portion 29 in which a raising stand 71 is provided. The space portion 29 communicates with an outside on the lateral side of the hard portion main body 27 via a distal opening portion 31 provided in a lateral surface of the hard portion main body 27.

As shown in FIG. 1B, the hard portion main body 27 is connected to a channel tube 33. A channel 35 is formed inside the channel tube 33. A distal end of the channel 35 communicates with the space portion 29. The channel 35 is isolated by the channel tube 33 from a content space portion 37 in which contents such as an imaging cable and a light guide tube extend. The channel 35 opens to an outside of the holding portion 50 at an insertion opening portion 39 provided in the holding portion 50.

As shown in FIG. 1B, the hard portion main body 27 is connected to a guide tube 41. The guide tube 41 extends through the insertion portion 20 along the longitudinal axis C direction. A guide channel (channel) 42 is formed inside the guide tube 41. A distal end of the guide channel 42 communicates with the space portion 29. A pulling and pressing member 85 extends through the guide channel 42. A distal end of the pulling and pressing member 85 is connected to the raising stand 71.

As shown in FIG. 1A, the holding portion 50 has a bend operation knob 51 that is a bend operation input portion to which a bend operation to bend the bendable portion 23 is input, a suction operation button 53, an gas and liquid supply operation button 55, and a raising operation portion 73 to raise the raising stand 71. One end of a universal cord 57 is connected to the holding portion 50. The other end of the universal cord 57 is connectable to unshown peripheral devices of the insertion apparatus 10.

[Raising Device 70]

As shown in FIG. 1A, FIG. 1B, and FIG. 1C, the insertion apparatus 10 further has a raising device 70 which raises the insert object to be inserted into the insertion portion 20, from the distal opening portion 31 provided at the distal end portion of the insertion portion 20.

As shown in FIG. 1A, FIG. 1B, and FIG. 1C, the raising device 70 has the raising stand 71 which can raise the insert object to be inserted into the insertion portion 20, from the distal opening portion 31 provided at the distal end portion of the insertion portion 20, and the raising operation portion 73 which is provided in the holding portion 50 coupled to the insertion portion 20 and which remotely operates the raising stand 71 to raise the raising stand 71. The raising device 70 further has a transmission mechanism 80 which is coupled to the raising stand 71 and the raising operation portion 73 and which transmits an operational force of the raising operation portion 73 to the raising stand 71 to raise the raising stand 71 by the rotation of the raising stand 71. The raising operation portion 73 and the transmission mechanism 80 function as a raising operation mechanism which operates the raising stand 71.

[Raising Stand 71]

As shown in FIG. 1B, the raising stand 71 is disposed in the space portion 29. The raising stand 71 is attached to the hard portion main body 27 in a state where the raising stand 71 is rotatable relative to the hard portion main body 27. The raising stand 71 switches the state of the raising stand 71 by rotation to either a raised state in which the raising stand 71 is exposed and raised to the outside from the distal opening portion 31 or a housed state (laid state) in which the raising stand 71 is housed in the space portion 29. The raising stand 71 controls the lead-out direction of the insert object for insertion through the channel 35 by the raised state. The raising stand 71 controls the lead-protrusion direction of the insert object by the raised state, and the insert object protrudes to the lateral side of the insertion portion 20 from the distal opening portion 31. In the housed state, the raising stand 71 is laid in the space portion 29.

As shown in FIG. 1B, the raising stand 71 has a curved guide surface to guide the insert object, and a raising shaft 71a which functions as a rotation shaft during raising. The raising shaft 71a is provided at the root (proximal end portion) of the raising stand 71. The raising shaft 71a is provided in the space portion 29, and provided along a direction that intersects at right angles with the longitudinal axis C. The raising stand 71 rotates on the raising shaft 71a by a desired angle around the raising shaft 71a. As a result of the rotation of the raising stand 71, the raising stand 71 is displaced in a direction in which the guide surface raises, and the insert object which is guided on the guide surface raises.

[Raising Operation Portion 73]

As shown in FIG. 1C, the raising operation portion 73 pulls or presses the raising stand 71 via the transmission mechanism 80. As shown in FIG. 1B and FIG. 1C, the raising operation portion 73 switches the raising stand 71 into the raised state by pulling, and switches the raising stand 71 into the housed state by pressing.

As shown in FIG. 1C, the raising operation portion 73 further has an operation lever 73a which is operated by an operator, and a coupling member 73b which is coupled to the operation lever 73a and the transmission mechanism 80 and which transmits the operational force input from the operation lever 73a to the transmission mechanism 80.

The operation lever 73a has a proximal end portion which functions as a knob and which extends to the outside of the holding portion 50, and a distal end portion which is provided inside the holding portion 50 and which has a rotation axis 731a provided along a direction that intersects at right angles with the longitudinal axis C.

The coupling member 73b has a proximal end portion which is coupled to the distal end portion of the operation lever 73a, and a distal end portion which is coupled to a proximal end portion of a mobile member 81 provided in the transmission mechanism 80. The coupling member 73b is a plate-shaped member. The coupling member 73b is provided inside the holding portion 50. The coupling member 73b may be included in the transmission mechanism 80.

The operation lever 73a is operated by the operator and thereby rotates around the rotation axis 731a. The rotational operation of the operation lever 73a is transmitted to the coupling member 73b, thereby the coupling member 73b moves forward and backward. A forward and backward operation of the coupling member 73b moves forward and backward the transmission mechanism 80. This forward and backward force is transmitted to the raising stand 71 via the transmission mechanism 80. Accordingly, the raising stand 71 rotates by the forward and backward force, and one of the raised state and the housed state is switched to the other by the rotation.

[Configuration 1 of Transmission Mechanism 80]

The transmission mechanism 80 is provided inside the holding portion 50 and inside the insertion portion 20.

As shown in FIG. 1C, FIG. 2A, FIG. 2C, and FIG. 2D, the transmission mechanism 80 has the mobile member 81 which moves forward and backward along the longitudinal axis C direction that is an axial direction of the transmission mechanism 80 by an operation of the raising operation portion 73, and an adjustment unit 83 which is coupled to the mobile member 81 and thus moves forward and backward along the longitudinal axis C direction together with the mobile member 81 and which varies in the adjustment amount in the longitudinal axis C direction as desired. The adjustment amount refers to, for example, the length of the adjustment unit 83 in the longitudinal axis C direction. The transmission mechanism 80 further has the pulling and pressing member 85 which is coupled to the raising stand 71 and the adjustment unit 83 in a state where tension adjusted by the adjustment amount as desired is acting and which pulls or presses the raising stand 71 in response to the forward and backward movement of the mobile member 81. The adjustment unit 83 adjusts the tension of the pulling and pressing member 85 by the adjustment amount.

[Mobile Member 81]

As shown in FIG. 1C, FIG. 2A, FIG. 2C, and FIG. 2D, the mobile member 81 has the proximal end portion which is coupled to the distal end portion of the coupling member 73b, and a distal end portion which is coupled to a proximal end portion of a later-described expansion and contraction member 83a that is a proximal end portion of the adjustment unit 83. The mobile member 81 is coupled to the coupling member 73b, and moves forward and backward along the longitudinal axis C direction in response to the forward and backward operation of the coupling member 73b. The mobile member 81 is provided along the longitudinal axis C direction.

[Adjustment Unit 83]

Figure 2A:
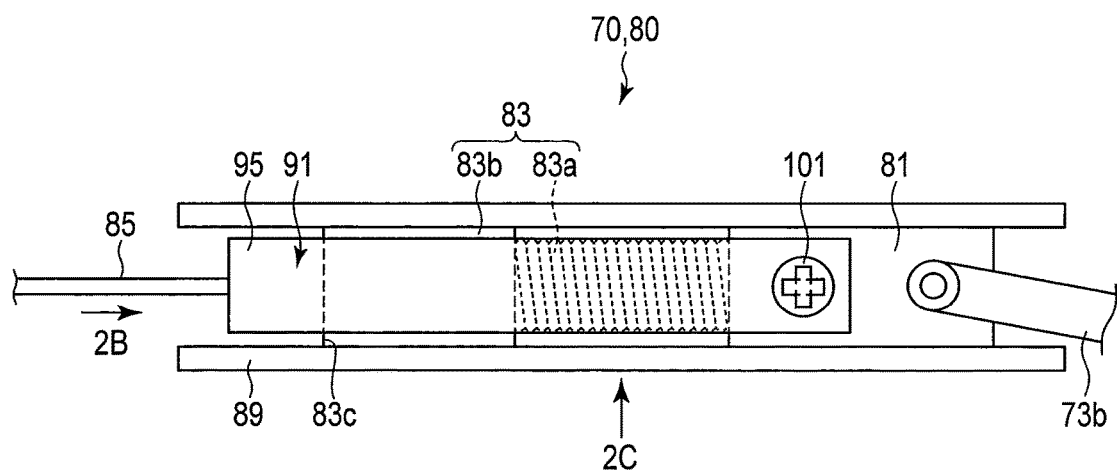
FIG. 2A is a top view of a transmission mechanism according to the first embodiment.
Figure 2B:
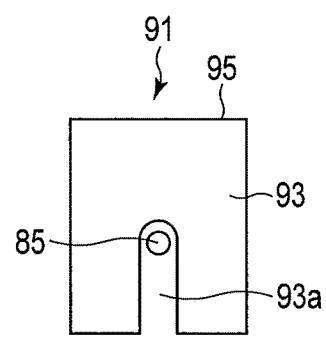
FIG. 2B is a front view of a regulation surface portion viewed from an arrow 2B side indicated in FIG. 2A.
Figure 2C:
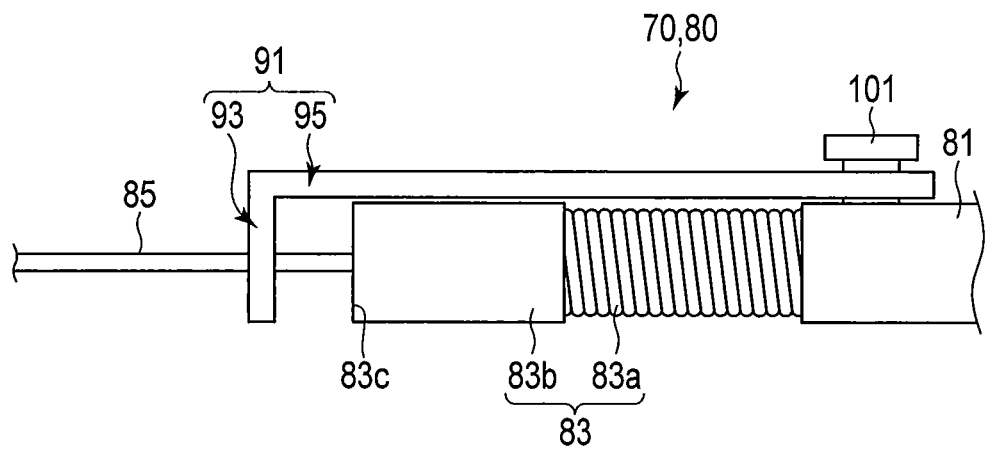
FIG. 2C is a side view of the transmission mechanism viewed from an arrow 2C side indicated in FIG. 2A in a state where a guide member shown in FIG. 2A is removed.
Figure 2D:
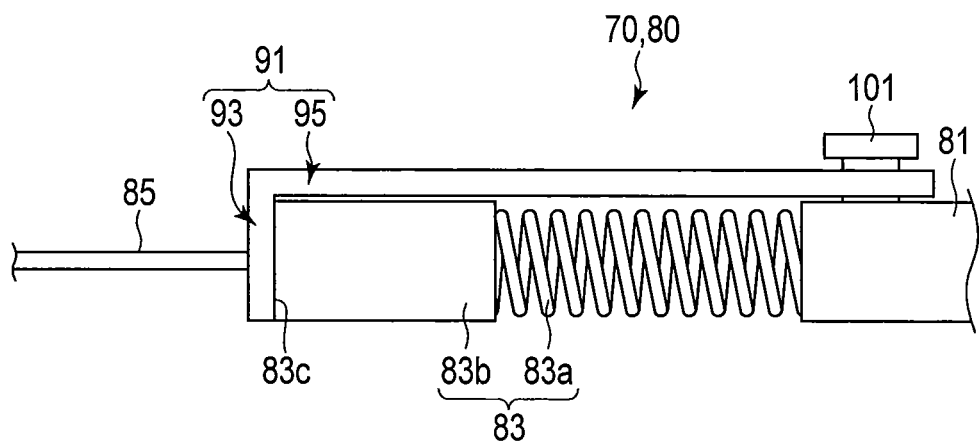
FIG. 2D is a diagram showing a state where an expansion and contraction member expands from a state shown in FIG. 2C, and the regulation surface portion contacts the coupling member whereby a regulation portion regulates the expansion of the expansion and contraction member.

As shown in FIG. 2C and FIG. 2D, in the present embodiment, for example, the length of the adjustment unit 83 in the longitudinal axis C direction varies, and the adjustment amount varies accordingly. This adjustment amount (length change) refers to a distance between the proximal end portion of the pulling and pressing member 85 and the distal end portion of the mobile member 81. The adjustment unit 83 adjusts the raise angle of the raising stand 71 by this adjustment amount.

As shown in FIG. 2A, FIG. 2C, and FIG. 2D, the adjustment unit 83 has the expansion and contraction member 83a which is coupled to the mobile member 81 and thus moves forward and backward along the longitudinal axis C direction together with the mobile member 81, and a coupling member 83b which is coupled to the expansion and contraction member 83a and the pulling and pressing member 85.

The expansion and contraction member 83a has the proximal end portion which is coupled to the distal end portion of the mobile member 81, and a distal end portion which is coupled to a proximal end portion of the coupling member 83b. The expansion and contraction member 83a is provided coaxially with the mobile member 81. The expansion and contraction member 83a moves forward and backward together with the mobile member 81 in response to the forward and backward movement of the mobile member 81. The expansion and contraction member 83a is provided along the longitudinal axis C direction.

As shown in FIG. 2C and FIG. 2D, the expansion and contraction member 83a expands and contracts along the longitudinal axis C direction. The expansion and contraction member 83a is a variable length member in which the length of the expansion and contraction member 83a in the longitudinal axis C direction varies by expansion and contraction. The expansion and contraction member 83a expands and contracts so that the coupling member 83b comes away from or comes closer to the mobile member 81 in the longitudinal axis C direction. The expansion and contraction member 83a expands and contracts to adjust the distance between the distal end portion of the mobile member 81 and the proximal end portion of the pulling and pressing member 85. The expansion and contraction member 83a is an adjustment member which adjusts the raise angle of the raising stand 71 via the tension of the pulling and pressing member 85 and the pulling and pressing member 85 by expansion and contraction. For example, the expansion and contraction member 83a contracts in the housed state and the raised state, and expands when the raising stand 71 receives the force from the insert object mounted on the raising stand 71 in the raised state. The expansion and contraction member 83a has, for example, at least one selected from the group consisting of a coil spring, a rubber bush, a pneumatic damper, and a hydraulic damper. The expansion and contraction member 83a may be formed by elastic bodies different in elastic force that are connected to one another.

As shown in FIG. 2A, FIG. 2C, and FIG. 2D, the coupling member 83b intervenes between the expansion and contraction member 83a and the pulling and pressing member 85 in the longitudinal axis C direction. The coupling member 83b has the proximal end portion which is coupled to the distal end portion of the expansion and contraction member 83a, and a distal end portion which is coupled to the proximal end portion of the pulling and pressing member 85. The coupling member 83b is provided coaxially with the expansion and contraction member 83a. The coupling member 83b is provided along the longitudinal axis C direction.

As shown in FIG. 2C and FIG. 2D, this coupling member 83b moves forward and backward along the longitudinal axis C direction together with the mobile member 81 and the expansion and contraction member 83a in response to the forward and backward movement of the mobile member 81 and the expansion and contraction member 83a, and moves toward the raising stand 71 from the expansion and contraction member 83a by the expansion of the expansion and contraction member 83a.

As shown in FIG. 2A, the coupling member 83b has a width which is substantially similar to that of the mobile member 81, and has a width which is greater than that of the pulling and pressing member 85. The coupling member 83b has a columnar shape. As shown in FIG. 2D, the coupling member 83b has a front surface 83c which functions as a flat surface portion which contacts a later-described regulation surface portion 93.

[Pulling and Pressing Member 85]

As shown in FIG. 1C, FIG. 2A, FIG. 2C, and FIG. 2D, the pulling and pressing member 85 intervenes between the coupling member 83b and the raising stand 71 in the longitudinal axis C direction. The pulling and pressing member 85 has the proximal end portion which is coupled to the distal end portion of the coupling member 83b, and a distal end portion which is directly coupled to the raising stand 71. The pulling and pressing member 85 is provided coaxially with the coupling member 83b. The pulling and pressing member 85 is provided along the longitudinal axis C direction.

The pulling and pressing member 85 moves forward and backward along the longitudinal axis C direction together with the mobile member 81 in response to the forward and backward movement of the mobile member 81. When the pulling and pressing member 85 directly presses the raising stand 71 toward the distal end of the distal end hard portion 25, the raising stand 71 is housed. When the pulling and pressing member 85 directly pulls the raising stand 71, the raising stand 71 raises. The pulling and pressing member 85 has a desired length between the coupling member 83b and the raising stand 71. Thus, in the housed state, tension always acts on the pulling and pressing member 85. The pulling and pressing member 85 presses the raising stand 71 by the tension in the housed state, and unintentional rising of the raising stand 71 is prevented. The pulling and pressing member 85 has a linear member such as a wire member. The pulling and pressing member 85 is bendable.

[Configuration 2 of Transmission Mechanism 80]

As shown in FIG. 2A, the transmission mechanism 80 further has a guide member 89 which guides the mobile member 81 and the coupling member 83b along the longitudinal axis C direction from both side surfaces of the mobile member 81 and the coupling member 83b so that the mobile member 81, the expansion and contraction member 83a, and the coupling member 83b move forward and backward along the longitudinal axis C direction. For example, a pair of guide members 89 are provided. Therefore, the inner width of the guide member 89 is substantially the same as the outer width of the mobile member 81 and the coupling member 83b. Thus, the mobile member 81 and the coupling member 83b slide on an inner surface of the guide member 89. The guide member 89 is provided inside the holding portion 50, and is fixed to the holding portion 50.

[Configuration 3 of Transmission Mechanism 80 (Regulation Portion 91)]

The raising operation portion 73 operates the raising stand 71 via the mobile member 81, the expansion and contraction member 83a, and the coupling member 83b, and the pulling and pressing member 85. The raising stand 71 is brought into the raised state or the housed state by this operation. In the raised state in which the raising stand 71 has raised while the insert object is mounted on the raising stand 71, the raising stand 71 receives the force from the insert object, and will fall down due to the force. This force pulls the expansion and contraction member 83a toward the raising stand 71 via the pulling and pressing member 85 and the coupling member 83b. If this force becomes greater than, for example, the spring constant of the expansion and contraction member 83a, the expansion and contraction member 83a which has contracted in the raised state expands. However, if the expansion and contraction member 83a expands to a maximum permissible expansion amount or more, i.e., if the expansion and contraction member 83a excessively expands, tension no longer acts on the pulling and pressing member 85. Therefore, the pulling and pressing member 85 bends, and when the raising stand 71 receives the force from the insert object, the raising stand 71 falls down due to this force. Thus, the raising stand 71 falls down if the adjustment unit 83 exceeds, for example, a maximum permissible adjustment amount.

Therefore, even if the raising operation portion 73 is performing the raising operation, the pulling and pressing member 85 is bent, and the raising stand 71 is not brought into the raised state. The maximum permissible adjustment amount refers to at least one of an adjustment amount that ensures the raised state suited to, for example, a treatment, and an adjustment amount that permits the expanded expansion and contraction member 83a to be restored to a state in which the expansion and contraction member 83a has contracted by a predetermined degree. The expansion and contraction member 83a which has expanded to the maximum permissible adjustment amount or more cannot be restored to an initial state in which, for example, the expansion and contraction member 83a has contracted by the predetermined degree. If the expansion and contraction member 83a expands to the maximum permissible adjustment amount or more, the raised state suited to, for example, a treatment is not maintained. The maximum permissible adjustment amount is also referred to as a maximum permissible length and the aforementioned maximum permissible expansion amount in the present embodiment.

Thus, as shown in FIG. 2A, FIG. 2C, and FIG. 2D, the transmission mechanism 80 further has a regulation portion 91 which regulates the adjustment amount of the adjustment unit 83 when the raising operation portion 73 is operated and when tension is applied to the adjustment unit 83. The regulation portion 91 moves forward and backward along the longitudinal axis C direction together with the mobile member 81. The regulation portion 91 regulates the adjustment amount of the adjustment unit 83 for the adjustment unit 83 which will exceed the maximum permissible adjustment amount due to the force that the raising stand 71 receives from the insert object in the raised state, and the regulation portion 91 can keep tension acting on the pulling and pressing member 85 in the raised state of the raising stand 71. As shown in FIG. 2D, in the present embodiment, the regulation portion 91 regulates (restricts) the expansion of the expansion and contraction member 83a for the expansion and contraction member 83a which will expand to the maximum permissible expansion amount of the expansion and contraction member 83a or more due to the force that the raising stand 71 receives from the insert in the raised state because the tension keeps acting on the pulling and pressing member 85 in the raised state of the raising stand 71.

As shown in FIG. 2A, FIG. 2C, and FIG. 2D, the regulation portion 91 has the regulation surface portion 93 which moves forward and backward in the axial direction together with the mobile member 81 and which regulates the expansion amount of the expansion and contraction member 83a that is the adjustment amount of the adjustment unit 83 by receiving the expansion of the expansion and contraction member 83a that is the adjustment of the adjustment unit 83. The regulation portion 91 has a support portion 95 which supports the regulation surface portion 93 in contact with the mobile member 81 so that the regulation surface portion 93 moves forward and backward together with the mobile member 81.

As shown in FIG. 2A, FIG. 2C, and FIG. 2D, in the present embodiment, the regulation surface portion 93 and the support portion 95 are continuous with each other, and, for example, the regulation surface portion 93 and the support portion 95 form an L-shape. The regulation surface portion 93 and the support portion 95 may be integral or separate if continuous with each other. The regulation surface portion 93 and the support portion 95 are made of a hard material such as a metal.

The support portion 95 is removably fixed to the mobile member 81 by, for example, a screw 101. Thus, the regulation surface portion 93 moves forward and backward in the axial direction together with the mobile member 81 due to the fixing, and contacts the coupling member 83b in a state where the regulation surface portion 93 is positioned and fixed at the mobile member 81 via the support portion 95. The support portion 95 is in indirect contact with the mobile member 81 via the screw 101. The support portion 95 may be fixed to the mobile member 81 via the screw 101 in contact with the upper surface of the mobile member 81.

[Regulation Surface Portion 93]

As shown in FIG. 2C and FIG. 2D, the regulation surface portion 93 is provided between the raising stand 71 and the coupling member 83b in the expansion and contraction direction of the expansion and contraction member 83a which is the longitudinal axis C direction. Thus, the regulation surface portion 93 is provided on the side where the coupling member 83b expands in the expansion and contraction direction, and is provided ahead of the coupling member 83b (on the raising stand 71 side). The regulation surface portion 93 is provided along a direction that intersects at right angles with the expansion and contraction direction, and contacts the coupling member 83b. The regulation surface portion 93 is provided coaxially with the coupling member 83b. The regulation surface portion 93 has substantially the same shape as the coupling member 83b.

As shown in FIG. 2C, the regulation surface portion 93 functions as a facing surface which faces the coupling member 83b in the longitudinal axis C direction in a state where the expansion and contraction member 83a has contracted, for example, in the housed state or the raised state.

As shown in FIG. 2D, the regulation surface portion 93 functions as a contact surface which contacts the coupling member 83b when the expansion and contraction member 83a expands to the maximum permissible expansion amount or more. In other words, the regulation surface portion 93 prevents the expansion and contraction member 83a from expanding to the maximum permissible expansion amount or more by the contact of the regulation surface portion 93 with the moving coupling member 83b toward the raising stand 71 due to the expansion of the expansion and contraction member 83a when the expansion and contraction member 83a expands to the maximum permissible expansion amount which is the maximum permissible adjustment amount or more. That is, the regulation surface portion 93 contacts the coupling member 83b and thereby functions as a stopper to prevent the coupling member 83b from going beyond, for example, a maximum permissible length position of the expansion and contraction member 83a. Thus, the regulation surface portion 93 regulates the expansion of the expansion and contraction member 83a via the coupling member 83b.

Here, when the raising stand 71 receives force from the insert object and will then fall down due to the force, this force which acts on the raising stand 71 from the insert object is referred to as force A.

When the expansion and contraction member 83a expands to the maximum permissible expansion amount so that the regulation surface portion 93 contacts the coupling member 83b, a reaction force of the regulation surface portion 93 against the coupling member 83b is referred to as reaction force B.

The force by which the expansion and contraction member 83a will contract when the regulation surface portion 93 contacts the coupling member 83b is referred to as force C.

In the above, the relation: force A=reaction force B+force C is satisfied.

The regulation surface portion 93 is made of a hard material and therefore has durability to be able to endure the difference between the force A and the force C.

The regulation surface portion 93 has a shape such that the regulation surface portion 93 is provided from above of the pulling and pressing member 85 and the pulling and pressing member 85 passes through the regulation surface portion 93 in the longitudinal axis C direction accordingly when the support portion 95 is fixed to the mobile member 81. As shown in FIG. 2B, such a regulation surface portion 93 has, for example, a U-shape. A diameter of a cutout portion 93a of the regulation surface portion 93 is substantially the same as a diameter of the pulling and pressing member 85.

[Support Portion 95]

As shown in FIG. 2A, FIG. 2C, and FIG. 2D, the support portion 95 is provided along the longitudinal axis C direction. The support portion 95 functions as a flat-plate-shaped frame. The support portion 95 has a proximal end portion which is fixed to a upper surface of the distal end portion of the mobile member 81 by, for example, the screw 101, and a distal end portion which is continuous with the regulation surface portion 93. When the proximal end portion is fixed to the mobile member 81, the support portion 95 is provided above the expansion and contraction member 83*a*, above the coupling member 83*b*, and above the proximal end portion of the pulling and pressing member 85. Such a support portion 95 functions as a lid-shaped member. When the proximal end portion is fixed to the mobile member 81, the support portion 95 is located a desired distance away from the expansion and contraction member 83*a*, the coupling member 83*b*, and the pulling and pressing member 85 in a height direction of the transmission mechanism 80. The support portion 95 including the regulation surface portion 93 becomes movable forward and backward along the longitudinal axis C direction together with the mobile member 81 when the proximal end portion of the support portion 95 is fixed to the mobile member 81.

As shown in FIG. 2A, the support portion 95 has a width smaller than the inner width of the guide member 89. As long as the support portion 95 including the regulation surface portion 93 is movable forward and backward together with the mobile member 81, the fixing position and fixing method of the support portion 95 are not specifically limited. Therefore, the support portion 95 may be provided under the mobile member 81, the expansion and contraction member 83*a*, and the coupling member 83*b*.

[Functions]

The insert object is inserted into the insertion portion 20 from the insertion opening portion 39. The insert object is inserted through the channel 35, and reaches the space portion 29. The insert object is then mounted on the raising stand 71 in the housed state. In this state, the operation lever 73*a* rotates. The rotational operation of the operation lever 73*a* is transmitted to the coupling member 73*b*, and then moves backward the coupling member 73*b*. The backward operation of the coupling member 73*b* moves backward the transmission mechanism 80.

In this instance, in the transmission mechanism 80, the mobile member 81 which is coupled to the coupling member 73*b*, the adjustment unit 83 and the regulation portion 91 which are coupled to the mobile member 81, and the pulling and pressing member 85 which is coupled to the adjustment unit 83 move backward together. The transmission mechanism 80 moves backward along the longitudinal axis C direction by the guide member 89.

This backward movement force is transmitted to the raising stand 71 via the transmission mechanism 80. That is, the raising stand 71 is pulled by the pulling and pressing member 85, and is switched to the raised state. As a result, the insert object raises from the distal opening portion 31 by the raising stand 71.

In this raised state, the raising stand 71 receives force from the insert object, and will fall down due to the force. This force pulls the expansion and contraction member 83*a* toward the raising stand 71 via the pulling and pressing member 85 and the coupling member 83*b*. If this force becomes greater than, for example, the spring constant of the expansion and contraction member 83*a*, the expansion and contraction member 83*a* which has contracted in the raise state expands due to the force that the raising stand 71 receives from the insert object. The coupling member 83*b* then moves toward the raising stand 71 from the expansion and contraction member 83*a* due to the expansion of the expansion and contraction member 83*a*.

In this instance, as shown in FIG. 2D, the regulation portion 91 regulates the expansion of the expansion and contraction member 83*a* for the expansion and contraction member 83*a* which will expand to the maximum permissible expansion amount of the expansion and contraction member 83*a* or more due to the force that the raising stand 71 receives from the insert object in the raised state. Specifically, the regulation surface portion 93 regulates the expansion of the expansion and contraction member 83*a* by receiving the expansion of the expansion and contraction member 83*a* via the coupling member 83*b*. In other words, the regulation surface portion 93 prevents the expansion and contraction member 83*a* from expanding to the maximum permissible expansion amount or more by the contact of the regulation surface portion 93 with the moving coupling member 83*b* toward the raising stand 71 due to the expansion of the expansion and contraction member 83*a* when the expansion and contraction member 83*a* expands to the maximum permissible expansion amount or more. The regulation surface portion 93 is provided coaxially with the coupling member 83*b*, and therefore contacts the coupling member 83*b* with certainty.

The support portion 95 is fixed to the mobile member 81. Thus, when the regulation surface portion 93 contacts the coupling member 83*b* and is pressed toward the raising stand 71 by the coupling member 83*b*, the relative displacement of the support portion 95 including the regulation surface portion 93 to the mobile member 81 is prevented. As a result, the expansion of the expansion and contraction member 83*a* to the maximum permissible expansion amount or more is prevented.

The force that the raising stand 71 receives from the insert object varies according to the thickness or hardness of the insert object. The position at which the regulation surface portion 93 contacts the coupling member 83*b* changes relative to for example, the raising stand 71 in the longitudinal axis C direction according to the thickness or hardness of the insert object. However, the support portion 95 including the regulation surface portion 93 is fixed to the mobile member 81, and is movable in the longitudinal axis C direction together with the mobile member 81. Thus, the expansion of the expansion and contraction member 83*a* to the maximum permissible expansion amount or more is prevented, and a regulated state is always maintained without the influence of the thickness and hardness of the insert object. This also applies to the case where the raising stand 71 which has raised further raises.

The regulation surface portion 93 and the support portion 95 are made of a hard material. Therefore, the regulation surface portion 93 and the support portion 95 can endure without breaking even when receiving force from the coupling member 83*b*.

This prevents the expansion and contraction member 83*a* from expanding to, for example, the maximum permissible expansion amount or more, i.e., prevents the expansion and contraction member 83*a* from excessively expanding. Therefore, the tension keeps acting on the pulling and pressing member 85 and bending of the pulling and pressing member 85 is prevented. Even when the raising stand 71 receives force from the insert object, the raising stand 71 is prevented from falling down due to the force. That is, even if the raising operation portion 73 is performing the raising operation, bending of the pulling and pressing member 85 is prevented. The raising stand 71 then maintains the raised state, and maintains a raise angle necessary for a treatment.

As described above, the regulation surface portion 93 prevents the expansion and contraction member 83*a* from expanding to the maximum permissible expansion amount or more. Thus, even if the raising operation is repeated, exhaustion of the expansion and contraction member 83a such as complete expansion of the expansion and contraction member 83a is prevented, the durability of the expansion and contraction member 83a is ensured.

Consequently, the raised state is maintained, a raise angle necessary for a treatment is maintained, and the shortage of a raise angle necessary for a treatment in the raised state is prevented. Because the regulation surface portion 93 is provided, a hard insert object can be used, and a suitable soft coil spring can be used as the expansion and contraction member 83a.

This can reduce reaction force received from the raising operation portion 73 when the operator operates the operation lever 73a to a maximum raised state in an expandable range of the expansion and contraction member 83a.

Because the regulation surface portion 93 is provided, the expansion of the expansion and contraction member 83a to the maximum permissible expansion amount or more is easily regulated even if the expansion and contraction member 83a freely moves together with the mobile member 81.

When, for example, a hard insert object is raised by the raising stand 71 in a state where the coupling member 83b is located away from the regulation surface portion 93, the insert object located in the vicinity of the raising stand 71 is bent. The bent insert object leans against the raising stand 71 to restore a straight state. Accordingly, the raising stand 71 receives force A1 from the insert object, and will thus fall down due to the force A1. This force A1 pulls the expansion and contraction member 83a toward the raising stand 71 via the pulling and pressing member 85 and the coupling member 83b. If this force A1 becomes greater than, for example, the spring constant of the expansion and contraction member 83a, the expansion and contraction member 83a which has contracted in the raised state expands due to the force that the raising stand 71 receives from the insert object.

In this instance, the force A1 acts on the pulling and pressing member 85, and pulls the pulling and pressing member 85 toward the raising stand 71. At the same time, the expanded expansion and contraction member 83a will contract, and force B1 by which the expansion and contraction member 83a will contract acts on the pulling and pressing member 85, and pulls the pulling and pressing member 85 toward the mobile member 81. The force A1 and the force B1 act in opposite directions. When the force A1 and the force B1 are evenly balanced, tension acts on the pulling and pressing member 85, and the raised state is maintained.

If the expansion and contraction member 83a and the coupling member 83b are not provided, for example, the pulling and pressing member 85 is directly coupled to the mobile member 81. Thus, the force A1 directly acts on the mobile member 81, and, for example, the mobile member 81 is therefore loaded. The expansion and contraction member 83a is provided as described above so that the force A1 is buffered by the expansion of the expansion and contraction member 83a, and loading of each member of the transmission mechanism 80, for example, the mobile member 81 is prevented. When the force A1 directly acts on the mobile member 81, the operator unconsciously operates the raising operation portion 73 to the maximum raised state and therefore feels strong a reaction force from the raising operation portion 73. However, the expansion and contraction member 83a expands so that the force A1 is buffered by the expansion of the expansion and contraction member 83a as described above, and the reaction force that the operator feels can be reduced. Even if the force A1 is greater than the force B1, the regulation surface portion 93 is provided and eliminates the difference between the force A1 and the force B1. Therefore, even if the force A1 is greater than the force B1, loading of each member of the transmission mechanism 80 is prevented.

If the expansion and contraction member 83a and the coupling member 83b are not provided, for example, the pulling and pressing member 85 is directly coupled to the mobile member 81. If the raised raising stand 71 further raises in a state where the force A1 is acting on the raising stand 71, excessive tension acts on, for example, the pulling and pressing member 85, and each part of the transmission mechanism 80 is loaded. However, in the present embodiment, the expansion and contraction member 83a is provided, and the expansion and contraction member 83a can expand in a state where the coupling member 83b is out of contact with the regulation surface portion 93 and the expansion and contraction member 83a has expanded. Thus, for example, the pulling and pressing member 85 can move forward due to, for example, the expansion of the expansion and contraction member 83a, and the action of excessive tension on the pulling and pressing member 85 is prevented. Thus, loading of each member of the transmission mechanism 80 is prevented, and the durability of the raising stand 71, the raising operation portion 73, and each member of the transmission mechanism 80 improves.

[Advantageous Effects]

As described above, in the present embodiment, the regulation portion 91 prevents the adjustment unit 83 from exceeding the maximum permissible adjustment amount. Specifically, the expansion of the expansion and contraction member 83a to the maximum permissible expansion amount or more is prevented. Thus, in the present embodiment, the durability of the adjustment unit 83 can be ensured, a raise angle necessary for a treatment can be maintained, and the insert object can be operated without the influence of the insert object and the adjustment unit 83.

In the present embodiment, the regulation surface portion 93 which functions as the contact surface is provided. Thus, in the present embodiment, the above can be achieved with certainty.

In the present embodiment, the regulation surface portion 93 does not directly contact the expansion and contraction member 83a, but contacts the coupling member 83b. Thus, in the present embodiment, surface contact can be ensured, and the above can be achieved with certainty. There is concern that if the expansion and contraction member 83a directly contacts the regulation surface portion 93, the expansion and contraction member 83a may break due to the contact. However, in the present embodiment, the coupling member 83b contacts the regulation surface portion 93, so that the breakage of the expansion and contraction member 83a can be prevented.

In the present embodiment, the regulation surface portion 93 is provided coaxially with the coupling member 83b. Thus, in the present embodiment, the regulation surface portion 93 can receive the expansion of the adjustment unit 83 with certainty.

In the present embodiment, the support portion 95 is fixed to the mobile member 81. Thus, in the present embodiment, when the regulation surface portion 93 contacts the coupling member 83b and is pressed toward the raising stand 71 by the coupling member 83b, the relative displacement of the support portion 95 including the regulation surface portion 93 to the mobile member 81 can be prevented. As a result, in the present embodiment, the expansion of the expansion and contraction member 83a to the maximum permissible expansion amount or more can be prevented.

In the present embodiment, the force that the raising stand 71 receives from the insert object varies according to the thickness or hardness of the insert object. The position at which the regulation surface portion 93 contacts the coupling member 83b changes relative to for example, the raising stand 71 in the longitudinal axis C direction according to the thickness or hardness of the insert object. However, in the present embodiment, the support portion 95 including the regulation surface portion 93 is fixed to the mobile member 81, and is movable in the longitudinal axis C direction together with the mobile member 81. Thus, the expansion of the expansion and contraction member 83a to the maximum permissible expansion amount or more can be prevented, and the regulated state can be always maintained without the influence of the thickness and hardness of the insert object.

In the present embodiment, the mobile member 81, the expansion and contraction member 83a, and the coupling member 83b can move forward and backward along the longitudinal axis C direction owing to the guide member 89.

The adjustment member may have a magnetic member which adjusts the distance between the distal end portion of the mobile member 81 and the proximal end portion of the pulling and pressing member 85 by magnetic force, instead of the expansion and contraction member 83a.

More than one expansion and contraction member 83a may be coaxially provided. In this case, the expansion and contraction forces (e.g., spring constants) of the expansion and contraction members 83a may be the same as or different from one another.

The insertion portion 20 functions as the insertion portion 20 of the insertion apparatus 10, and the raising stand 71 raises the insert object including, for example, the treatment instrument and the guide member, which, however, does not need to be limited. The insertion portion 20 may functions as an over tube, and the raising stand 71 may raise the insertion portion 20 of the endoscope to be inserted into the over tube. Thus, the raising stand 71 has only to raise insert object such as the treatment instrument to be inserted into the insertion portion 20, the guide member, and the insertion portion 20.

[Second Embodiment]

Figure 3A:
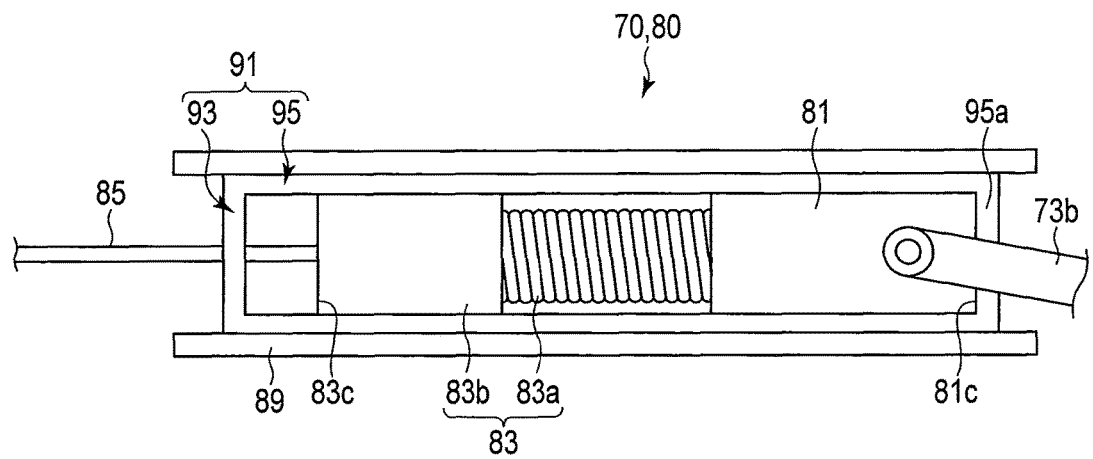
FIG. 3A is a top view of the transmission mechanism according to a second embodiment.
Figure 3B:
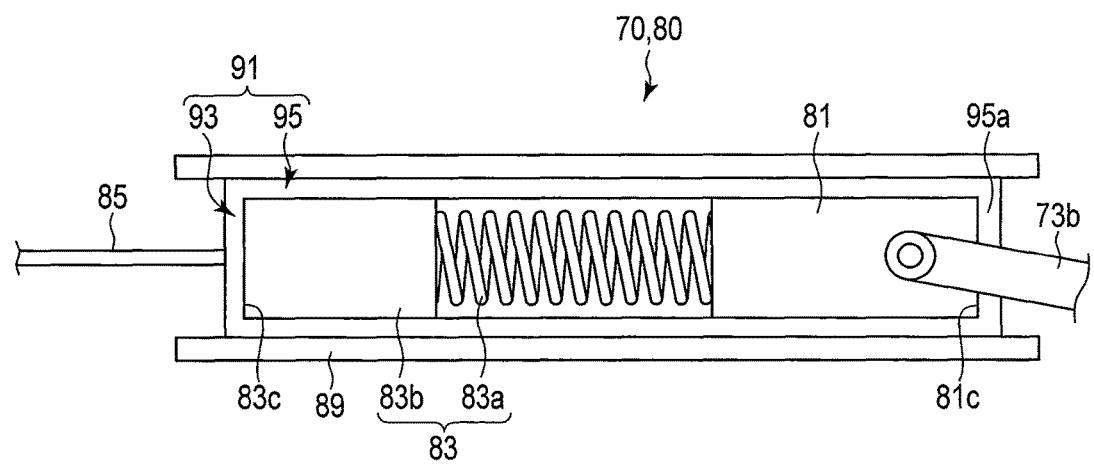
FIG. 3B is a diagram showing a state where the expansion and contraction member expands from a state shown in FIG. 3A, and the regulation surface portion contacts the coupling member whereby the regulation portion regulates the expansion of the expansion and contraction member.

Only the differences between the first embodiment and the second embodiment are described below with reference to FIG. 3A and FIG. 3B.

[Configuration]

The support portion 95 surrounds the mobile member 81, the expansion and contraction member 83a, and the coupling member 83b as one unit. The support portion 95 surrounds the front surfaces, back surfaces, and both side surfaces of these members. Such a support portion 95 has a frame shape. In other words, the mobile member 81, the expansion and contraction member 83a, and the coupling member 83b are provided inside one common support portion 95. The support portion 95 has an inner width which is substantially the same as the width of the mobile member 81 and the width of the coupling member 83b.

In the present embodiment, the regulation surface portion 93 functions as the front surface of the support portion 95. As shown in FIG. 3B, the support portion 95 has such a length that a back surface 95a of the support portion 95 contacts a back surface 81c of the mobile member 81 when the expansion and contraction member 83a expands to the maximum permissible expansion amount or more and the regulation surface portion 93 thus contacts the coupling member 83b.

When the mobile member 81 moves backward by the operation of the raising operation portion 73, the mobile member 81 pulls the support portion 95 backward in a state where the back surface 81c of the mobile member 81 is in contact with the back surface 95a of the support portion 95, so that the support portion 95 including the regulation surface portion 93 moves backward together with the mobile member 81.

When the mobile member 81 moves forward by the operation of the raising operation portion 73, the coupling member 83b presses the support portion 95 forward in a state where the front surface 83c of the coupling member 83b is in contact with the regulation surface portion 93 which functions as a front surface of the support portion 95, so that the support portion 95 including the regulation surface portion 93 moves forward together with the coupling member 83b.

Thus, the support portion 95 including the regulation surface portion 93 is movable back and forth along the longitudinal axis C direction together with the mobile member 81.

The support portion 95 has an outer width which is substantially the same as the inner width of the guide member 89. Thus, the outer circumferential surface of the support portion 95 is in contact with the inner surface of the guide member 89. When the support portion 95 moves forward and backward, the support portion 95 slides on the inner surface of the guide member 89. In this case, in the present embodiment, the guide member 89 guides the mobile member 81 and the coupling member 83b along the axial direction from both side surfaces of the mobile member 81 and the coupling member 83b via the support portion 95 so that the mobile member 81, the expansion and contraction member 83a, and the coupling member 83b move forward and backward along the axial direction.

As long as the support portion 95 including the regulation surface portion 93 is movable forward and backward along the longitudinal axis C direction together with the mobile member 81, the support portion 95 may be fixed to the mobile member 81 as in the first embodiment.

The regulation surface portion 93 contacts the coupling member 83b when the expansion and contraction member 83a expands to the maximum permissible expansion amount or more.

In this state, the back surface 81c of the mobile member 81 contacts the back surface 95a of the support portion 95. The shape of the support portion 95 is invariable, so that even if the coupling member 83b attempts to press the support portion 95 forward via the regulation surface portion 93, the forward movement of the support portion 95 is prevented by this contact. Therefore, the regulation surface portion 93 prevents the coupling member 83b from going beyond, for example, the maximum permissible length position of the expansion and contraction member 83a.

[Advantageous Effects]

In the present embodiment, the support portion 95 has a frame shape, and surrounds the mobile member 81, the expansion and contraction member 83a, and the coupling member 83b. Thus, in the present embodiment, the support portion 95 can be easily provided.

In the present embodiment, when the expansion and contraction member 83a expands to the maximum permissible expansion amount or more and the regulation surface portion 93 thus contacts the coupling member 83b, the back surface 95a of the support portion 95 comes into surface contact with the back surface 81c of the mobile member 81, and surface contact is conducted by this contact. Thus, in the present embodiment, when the regulation surface portion 93 contacts the coupling member 83b and is pressed by the coupling member 83b, the relative displacement of the support portion 95 including the regulation surface portion 93 to the mobile member 81 can be prevented. As a result, in the present embodiment, the expansion of the expansion and contraction member 83a to the maximum permissible expansion amount or more can be prevented with certainty. In the present embodiment, stress concentration can be avoided in the support portion 95 by the surface contact, and stress can be dispersed in the support portion 95. Thus, in the present embodiment, the strength of the support portion 95 including the regulation surface portion 93 can be improved.

In the present embodiment, when the support portion 95 moves, the back surface 81c of the mobile member 81 contacts the back surface 95a of the support portion 95, and the front surface 83c of the coupling member 83b contacts the front surface (the regulation surface portion 93) of the support portion 95. Thus, in the present embodiment, the regulation portion 91 including the regulation surface portion 93 can move forward and backward together with the mobile member 81 with certainty. When the support portion 95 moves, surface contact is conducted, so that stress concentration caused by the movement can be avoided, and stress can be dispersed. Thus, in the present embodiment, the strength of the support portion 95 including the regulation surface portion 93 can be improved.

For example, one of an outer circumferential surface of the coupling member 83b and an inner circumferential surface of the support portion 95 may have a protruding portion, and the other of the outer circumferential surface of the coupling member 83b and the inner circumferential surface of the support portion 95 may have an unshown slit portion into which the protruding portion is inserted. The slit portion is provided along the longitudinal axis C direction, and has the same length as the length of the movement of the coupling member 83b relative to the support portion 95. The protruding portion is shorter than the slit portion. When the coupling member 83b moves relative to the support portion 95, the protruding portion slides on the slit portion. Thus, the coupling member 83b can move along the longitudinal axis C direction with certainty. The protruding portion abuts on an end of the slit portion so that the regulation of the regulation surface portion 93 is assisted.

[First Modification of Second Embodiment]
[Configuration]
Only the differences between the second embodiment and a first modification are described below with reference to FIG. 4A, FIG. 4B, and FIG. 4C.

The guide member 89 has slit portions 89a which are provided on both side surfaces of the guide member 89 and into which both side surfaces of the support portion 95 are inserted. The slit portions 89a function as long groove portions provided along the longitudinal axis C direction. The slit portions 89a face each other. The slit portions 89a are longer than the movement length of the transmission mechanism 80.

[Advantageous Effects]
In the present modification, the support portion 95 is inserted into the slit portions 89a, and the transmission mechanism 80 can therefore be reduced in size and weight. The slit portion 89a may be provided in only one of the guide members 89.

[Third Embodiment]
[Configuration]
Only the differences between the second embodiment and the third embodiment are described below with reference to FIG. 5A, FIG. 5B, FIG. 5C, FIG. 5D, and FIG. 5E.

As shown in FIG. 5A, FIG. 5B, and FIG. 5C, the support portion 95 is attached to the mobile member 81 from the upper side of the mobile member 81, the expansion and contraction member 83a, and the coupling member 83b. Thus, the support portion 95 surrounds the upper part and side parts of the mobile member 81, the upper part of the expansion and contraction member 83a, and the upper part, side parts, and front part of the coupling member 83b. Such a support portion 95 is formed as a semi-cylindrical member having a bottom surface which functions as the regulation surface portion 93 and a cutout portion provided to expose the expansion and contraction member 83a to an outside.

As shown in FIG. 5A, FIG. 5B, and FIG. 5C, the support portion 95 has an upper surface portion 95c which functions as a flat-plate-shaped frame provided along the longitudinal axis C direction and which covers the upper parts of the mobile member 81, the expansion and contraction member 83a, and the coupling member 83b, extension portions 95d which are continuous with a proximal end portion of the upper surface portion 95c and which extend along a direction that intersects at right angles with the longitudinal axis C direction, and claw portions 95e provided at a distal end portions of the extension portions 95d.

The extension portions 95d catch the mobile member 81 therebetween, and the support portion 95 including the regulation surface portion 93 moves forward and backward together with the mobile member 81 by catching. The extension portions 95d are provided apart from each other by the width of the mobile member 81. For example, a pair of extension portions 95d are provided.

The claw portions 95e are caught on a catching portion 81a provided on a bottom surface side of the mobile member 81. Consequently, the support portion 95 including the regulation surface portion 93 does not come off the transmission mechanism 80 including the mobile member 81.

Such a support portion 95 is attached to the mobile member 81 from the upper surfaces of the mobile member 81, the expansion and contraction member 83a, and the coupling member 83b via the extension portions 95d and the claw portions 95e.

Figure 5D:
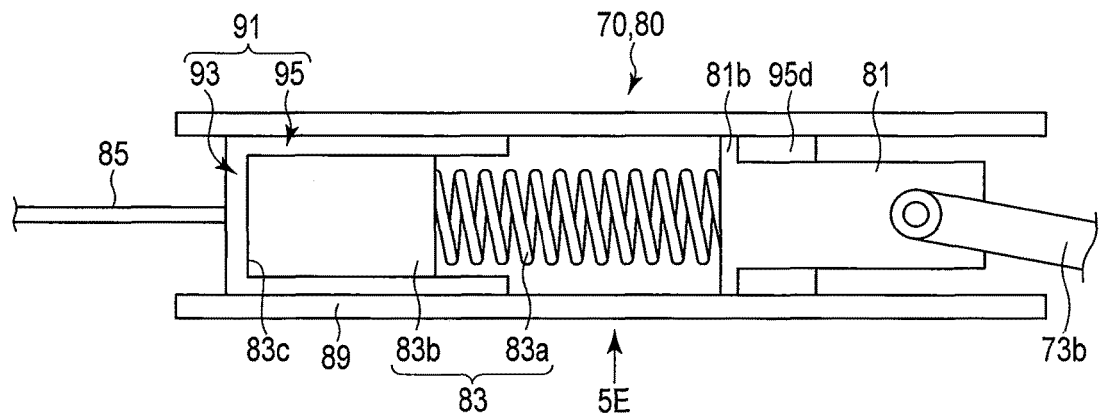
FIG. 5D is a diagram in which a top view of the regulation portion is omitted, showing a state where the expansion and contraction member expands from a state shown in FIG. 5A, and the regulation surface portion contacts the coupling member whereby the regulation portion regulates the expansion of the expansion and contraction member.
Figure 5E:
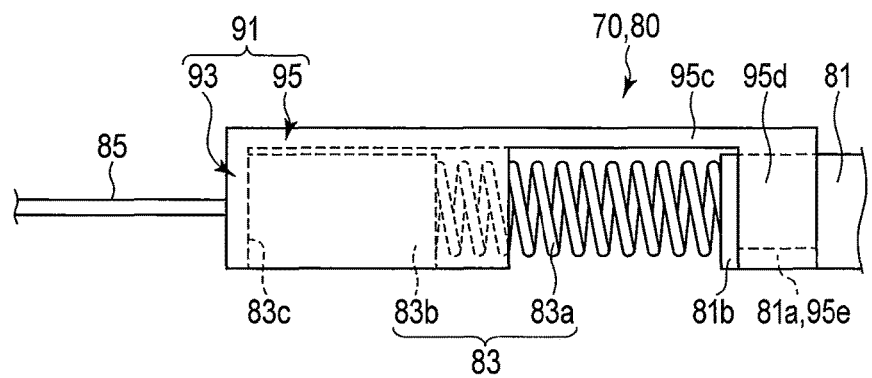
FIG. 5E is a diagram showing a state where the expansion and contraction member expands from a state shown in FIG. 5C, and the regulation surface portion contacts the coupling member whereby the regulation portion regulates the expansion of the expansion and contraction member.

As shown in FIG. 5D and FIG. 5E, the mobile member 81 has a protruding portion 81b which contacts the extension portions 95d when the mobile member 81 moves backward by the operation of the raising operation portion 73. When the support portion 95 is attached to the mobile member 81 via the extension portions 95d and the claw portions 95e, the protruding portion 81b is provided ahead of the extension portions 95d. When the mobile member 81 moves backward by the operation of the raising operation portion 73, the mobile member 81 pulls the support portion 95 backward so that the protruding portion 81b contacts the extension portions 95d, and the support portion 95 including the regulation surface portion 93 moves backward together with the mobile member 81 due to the contact. The protruding portion 81b is provided on the outer circumferential surface of the mobile member 81, and is a part of the outer circumferential surface protruding toward the lateral side of the mobile member 81 from the outer circumferential surface. The protruding portion 81b is provided, for example, all around the outer circumferential surface.

The support portion 95 has such a length that the extension portions 95d contact the protruding portion 81b of the mobile member 81 when the regulation surface portion 93 contacts the front surface 83c of the coupling member 83b. Thus, when the expansion and contraction member 83a expands, the extension portions 95d contact the protruding portion 81b, and the coupling member 83b contacts the regulation surface portion 93, so that the regulation surface portion 93 prevents the expansion and contraction member 83a from expanding to the maximum permissible expansion amount or more. When the coupling member 83b contacts the regulation surface portion 93, the extension portions 95d contact the protruding portion 81b. The two contacts take place at substantially the same timing.

When the mobile member 81 moves forward by the operation of the raising operation portion 73, the coupling member 83b presses the support portion 95 forward in a state where the front surface 83c of the coupling member 83b is in contact with the regulation surface portion 93, so that the support portion 95 including the regulation surface portion 93 moves forward together with the mobile member 81 due to the pressing.

Thus, the support portion 95 including the regulation surface portion 93 is movable forward and backward along the longitudinal axis C direction together with the mobile member 81.

As shown in FIG. 5A, the support portion 95 has an outer width which is substantially the same as the inner width of the guide member 89. Thus, the outer circumferential surface of the support portion 95 is in contact with the inner surface of the guide member 89. When the support portion 95 movies forward and backward, the support portion 95 slides on the inner surface of the guide member 89. In this case, in the present embodiment, the guide member 89 guides the mobile member 81 and the coupling member 83b along the axial direction from both side surfaces of the mobile member 81 and the coupling member 83b via the support portion 95. Accordingly, the mobile member 81, the expansion and contraction member 83a, and the coupling member 83b move forward and backward along the axial direction under the guidance.

The regulation surface portion 93 contacts the coupling member 83b when the expansion and contraction member 83a expands to the maximum permissible expansion amount or more.

In this state, the extension portions 95d contact the protruding portion 81b. The shape of the support portion 95 is invariable, so that even if the coupling member 83b attempts to press the support portion 95 forward via the regulation surface portion 93, the forward movement of the support portion 95 is prevented by this contact. Therefore, the regulation surface portion 93 prevents the coupling member 83b from exceeding, for example, the maximum permissible length position of the expansion and contraction member 83a.

[Advantageous Effects]

In the present embodiment, the support portion 95 is formed as the semi-cylindrical member having the bottom surface and the cutout portion, and the support portion 95 has the upper surface portion 95c, the extension portions 95d, and the claw portions 95e. The support portion 95 is attached to the mobile member 81 from the upper surfaces of the mobile member 81, the expansion and contraction member 83a, and the coupling member 83b via the extension portions 95d and the claw portions 95e. Thus, in the present embodiment, assemblability of the transmission mechanism 80 can be improved.

In the present embodiment, the regulation portion 91 can be easily attached to the mobile member 81 by the extension portions 95d and the claw portions 95e. In the present embodiment, the regulation portion 91 including the regulation surface portion 93 can move forward and backward together with the mobile member 81 with certainty and with ease owing to the extension portions 95d and the claw portions 95e.

In the present embodiment, when the expansion and contraction member 83a expands to the maximum permissible expansion amount or more and the regulation surface portion 93 thus contacts the coupling member 83b, the extension portions 95d contact the protruding portion 81b. Thus, in the present embodiment, when the regulation surface portion 93 contacts the coupling member 83b and is pressed by the coupling member 83b, the relative displacement of the support portion 95 including the regulation surface portion 93 to the mobile member 81 can be prevented. As a result, in the present embodiment, the expansion of the expansion and contraction member 83a to the maximum permissible expansion amount or more can be prevented with certainty.

According to the present embodiment, as the expansion and contraction member 83a, a relatively soft spring can also be used, and a spring having hardness suited to the inhibition of the diametrical increase of the insertion portion 20 and the operation of the raising stand can also be selected.

The present invention is not completely limited to the embodiments described above, and modifications of components can be made at the stage of carrying out the invention without departing from the spirit thereof. Various inventions can be made by properly combining the components disclosed in the embodiments described above.

What is claimed is:

1. A transmission mechanism configured to be coupled to each of a raising stand that raises and a raising operation portion to operate a raise of the raising stand and to transmit an operational force of the raising operation portion to the raising stand, the transmission mechanism comprising:
    a movable member which moves forward and backward along an axial direction of the transmission mechanism by an operation of the raising operation portion;
    an adjustment unit which is coupled to the movable member and moves forward and backward along the axial direction together with the movable member and which comprises an expansion and contraction member that changes in length in the axial direction;
    an elongated member coupled to the raising stand and the adjustment unit in a state where tension adjusted by the change of the length of the expansion and contraction member is acting thereon and which pulls or presses the raising stand;
    a regulation surface portion which contacts the adjustment unit; and
    a support portion which is provided in contact with the movable member and which moves the regulation surface portion forward and backward together with the movable member to support the regulation surface portion at a position to regulate the change of the length of the expansion and contraction member when the raising operation portion is operated and when tension is applied to the adjustment unit and the length of the expansion and contraction member changes.

2. The transmission mechanism according to claim 1, wherein the regulation surface portion and the support portion are configured to regulate the change of the length of the expansion and contraction member for the adjustment unit in which the raising stand is in a raised state and in which the length of the expansion and contraction member will exceed a maximum permissible expansion amount, and keep the tension acting on the elongated member in the raised state of the raising stand.

3. The transmission mechanism according to claim 1, wherein the regulation surface portion and the support portion are continuous with each other, and the support portion is removably fixed to the movable member.

4. The transmission mechanism according to claim 3, wherein the adjustment unit comprises a coupling member which is coupled to the expansion and contraction member and the elongated member and which moves forward and backward along the axial direction together with the movable member and the expansion and contraction member, and the transmission mechanism further comprises a guide member which guides the movable member and the coupling member along the axial direction.

5. The transmission mechanism according to claim 4, wherein the support portion surrounds the movable member, the expansion and contraction member, and the coupling member as one unit, and the support portion has such a length that a back surface of the support portion contacts a back surface of the movable member when the regulation surface portion contacts the coupling member.

6. The transmission mechanism according to claim 5, wherein when the movable member moves backward by the operation of the raising operation portion, the movable member pulls the support portion backward in a state where the back surface of the movable member is in contact with the back surface of the support portion, so that the support portion including the regulation surface portion moves backward together with the movable member, and when the movable member moves forward by the operation of the raising operation portion, the coupling member presses the support portion forward in a state where a front surface of the coupling member is in contact with the regulation surface portion which functions as a front surface of the support portion, so that the support portion including the regulation surface portion moves forward together with the movable member.

7. The transmission mechanism according to claim 6, wherein the guide member is configured to guide the movable member and the coupling member along the axial direction via the support portion.

8. The transmission mechanism according to claim 7, wherein the guide member comprises a slit portion into which side surfaces of the support portion are inserted.

9. The transmission mechanism according to claim 6, wherein the support portion comprises an upper surface portion which functions as a flat-plate-shaped frame provided along the axial direction and which covers the upper parts of the movable member, the expansion and contraction member, and the coupling member, a pair of extension portions which are continuous with a proximal end portion of the upper surface portion and which extend along a direction that intersects at right angles with the axial direction and which catch the movable member therebetween, and claw portions which are provided at a distal end portions of the extension portions and which are caught on a catching portion provided on a bottom surface side of the movable member.

10. The transmission mechanism according to claim 9, wherein the adjustment unit comprises a coupling member which is coupled to the expansion and contraction member and the elongated member and which moves forward and backward along the axial direction together with the movable member and the expansion and contraction member, and the regulation surface portion is provided between the raising stand and the coupling member in an expansion and contraction direction of the expansion and contraction member.

11. The transmission mechanism according to claim 10, wherein when the expansion and contraction member expands to a predetermined permissible expansion amount, the regulation surface portion prevents the expansion and contraction member from expanding more than the predetermined permissible expansion amount by the contact of the regulation surface portion with the coupling member which moves toward the raising stand due to the expansion of the expansion and contraction member.

12. The transmission mechanism according to claim 9, wherein the support portion has such a length that the extension portions contact a protruding portion of the movable member when the regulation surface portion contacts the coupling member.

13. The transmission mechanism according to claim 9, wherein when the movable member moves backward by the operation of the raising operation portion, the movable member pulls the support portion backward so that a protruding portion of the movable member contacts the extension portions, and the support portion including the regulation surface portion moves backward together with the movable member due to the contact, and when the movable member moves forward by the operation of the raising operation portion, the coupling member presses the support portion forward in a state where the front surface of the coupling member is in contact with the regulation surface portion which functions as a front surface of the support portion, so that the support portion including the regulation surface portion moves forward together with the movable member due to the pressing.

14. A raising device comprising:

the raising stand;

the raising operation portion; and the transmission mechanism according to claim 1.

15. An insertion apparatus comprising:

an insertion portion;

a holding portion provided at a proximal end portion of the insertion portion; and the raising device according to claim 14;

wherein the raising stand is provided inside a distal end portion of the insertion portion;

the raising operation portion is provided at the holding portion; and the transmission mechanism is provided inside the holding portion and inside the insertion portion.

* * * * *